United States Patent [19]

Place et al.

[11] 4,286,593
[45] Sep. 1, 1981

[54] VAGINAL CONTRACEPTIVE SHIELD

[76] Inventors: Virgil A. Place, 91 Hillbrook Dr., Portola Valley, Calif. 94025; Harold L. Crow, 25 E. 83rd St., New York, N.Y. 10028

[21] Appl. No.: 146,834

[22] Filed: May 5, 1980

[51] Int. Cl.³ .............................................. A61M 7/00
[52] U.S. Cl. ................... 128/260; 128/127; 128/270
[58] Field of Search ............... 128/127, 130, 260, 270, 128/285

[56] References Cited

U.S. PATENT DOCUMENTS

| | | | |
|---|---|---|---|
| 1,819,549 | 8/1931 | Fiessler | 128/127 |
| 2,234,495 | 3/1941 | Lay | 128/127 |
| 3,845,766 | 11/1974 | Zöller | 128/127 |
| 3,995,633 | 12/1976 | Gougen | 128/127 |
| 3,995,634 | 12/1976 | Drobish | 128/130 |
| 4,155,991 | 5/1979 | Schopflin et al. | 128/130 |
| 4,219,016 | 8/1980 | Drobish et al. | 128/130 |
| 4,228,797 | 10/1980 | Dickey | 128/270 |

OTHER PUBLICATIONS

*The Merck Index*, 9th Ed. Merck & Co., Inc., 1976, Rahway, N.J. p. 866.

*Primary Examiner*—C. Fred Rosenbaum
*Attorney, Agent, or Firm*—Bertram I. Rowland

[57] ABSTRACT

A flexible contraceptive vaginal shield having a supporting structure with an outer ring and an internal member which may comprise one or more concentric rings with or without a plurality of ribs connecting the rings said structure bonded to a flexible non-elastomeric film. A spermicide is normally applied to both sides of the film. The bonding of the supporting structure to the film is preferably by heat sealing. Spermicide applied to the ring side of the film is retained within reservoirs formed by the rings, the ribs and the film. In addition there may be reservoirs formed within the supporting structure that release spermicide through the flexing action caused by sexual intercourse.

20 Claims, 6 Drawing Figures

U.S. Patent  Sep. 1, 1981  Sheet 1 of 2  4,286,593
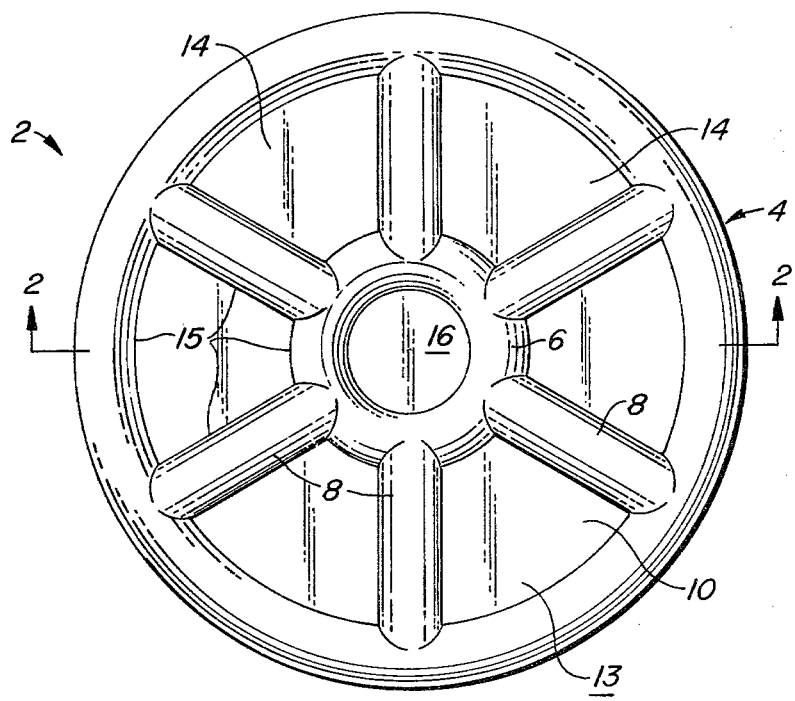
FIG._1.
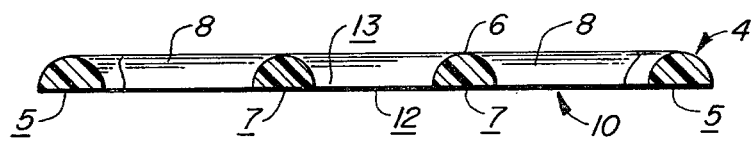
FIG._2.
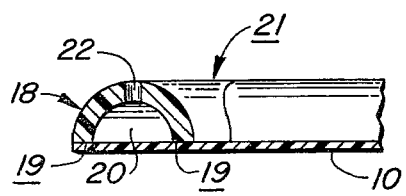
FIG._4.
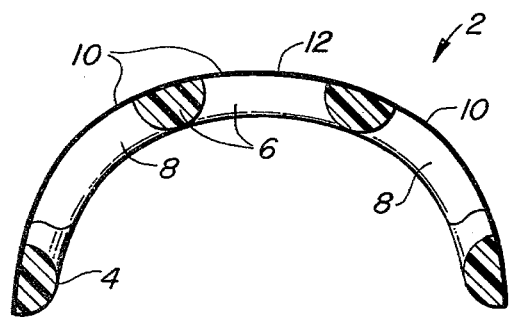
FIG._3.
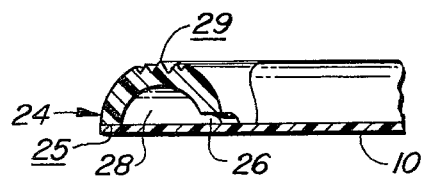
FIG._5.

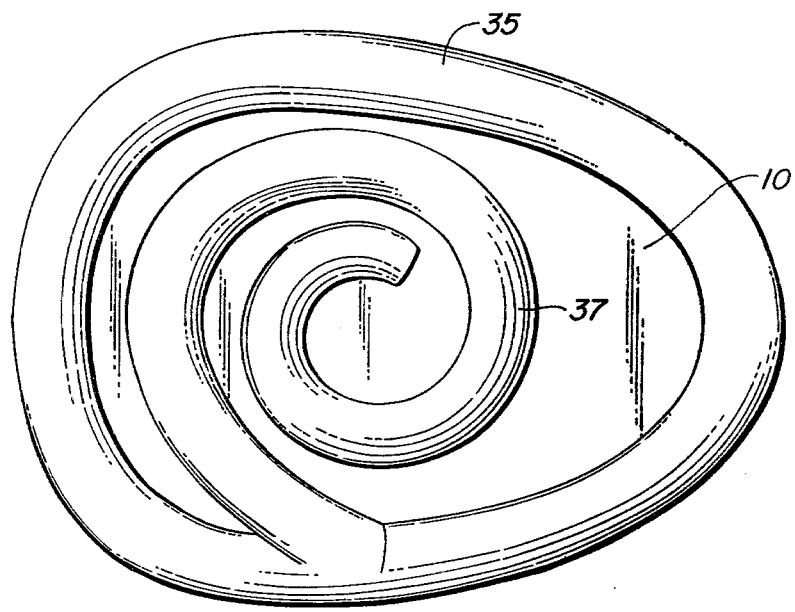
FIG._6.

VAGINAL CONTRACEPTIVE SHIELD

This inventon relates to vaginal contraceptives, herein termed medicated vaginal shield contraceptive which through its specific configuration provides optimum placement and distribution of spermicide.

BACKGROUND OF THE INVENTION

1. Field of the Invention

Vaginal contraceptives in the form of spermicides have been used for over 3800 years. Ancient vaginal contraceptives were often highly acidic substances carried by a pasty or sticky base and had some effect in immobilizing sperm. Presently, spermicides are available in various forms such as creams, foams, jellies, foaming tablets, suppositories, and films. However, all of these spermicides, regardless of their form, suffer from the same primary disadvantage of being difficult to properly distribute within the vagina, especially near the cervix. Further, the spermicides are often messy, have a tendency to run out of the vagina when the user is standing and often are not readily acceptable for use because their application usually interrupts the normal flow of events. They generally do not heighten, but rather diminish, the pleasurable aspects flowing from such physical activity.

2. Description of the Prior Art

Pessaries are used either to support the interior walls of the vagina or as a contraceptive to cover the cervix of the uterus. When used as a contraceptive, pessaries typically takes the form of a domed diaphragm for the application of a spermicide. An example of a domed contraceptive pessary is shown in U.S. Pat. No. 3,015,598. Pessaries intended to support the vaginal walls must be stiff enough to provide the mechanical support needed. Such a support pessary is disclosed by U.S. Pat. No. 2,234,495. As noted in such patent, resilient metallic springs are generally required to produce a pessary which is sufficiently stiff as well as resilient to provide the required mechanical support. Other U.S. patents which may be of interest are Nos. 2,141,040; 2,580,133; 3,216,422; 3,983,874; 3,995,663; and 4,093,490.

SUMMARY OF THE INVENTION

The present invention discloses a device which effectively distributes spermicide within the vagina before and during coitus through the unique vaginal shield configuration. The subject vaginal shield device acts as a physical and chemical barrier to conception. The device includes a relatively thick flexible supporting rib structure bound to a relatively thin flexible non-elastomeric film, where the ribs are substantially rod shaped. The supporting structure includes a circumferential rib extending around the perimeter of the film and an internal rib structure which may be of a variety of shapes and will usually be connected to the circumferential member at at least one point. The rib structure in conjunction with the film provides at least one storage area or reservoir for a spermidical composition.

The supporting rib structure may be on one or both sides of the film and is of sufficient thickness to maintain the film in extended form in a plane. When bent into a U configuration for introduction into the vaginal cavity, the rib structure maintains the film under sufficient tension to keep the film and spermicide in juxtaposition to the vaginal wall.

The ribs are rod-like in shape having circular, semicircular, parabolic or similar shape. The ribs should not have sharp edges although the surface may be mildly roughened. Desireably, the rib has a flat under-surface and an exposed rounded upper or outer surface. The vaginal shield in one manifestation may have one or more internal circular ribs (rings) concentric with the outer circular rib having a plurality of linear ribs connecting them. The rib structure may be formed by injection moulding and bonded to a thin flexible film, typically by heat sealing or at the moment of moulding the rings and ribs. In other configurations there may be one or more rings with or without ribs. Other structural shapes may be employed for internal support, such as spirals or crescent shapes. One purpose of these ribs is to incorporate the plastic memory of the planar surface, so that when the shield is bent into a U-configuration, energy is continually exerted to urge the planar surface to reassume its original planar configuration. In this way throughout coitus a continuous and gentle but firm pressure is maintained with resulting intimate contact with the vaginal wall. Another purpose is to partially define reservoirs for spermicide.

The ribs may be produced from a variety of polymeric materials such as polyethylene or ethylene-vinyl acetate copolymers. The film to which the ribs are bonded is typically the same flexible material from which the ribs are made. The material chosen must be physiologically acceptable and preferably be heat sealable or extrudable. The bonded structure has a spermicide, such as nonoxynol 9, by itself or in combination with other materials such as polyethylene glycols, applied to both sides. The composition employed should be gel-like and adhere to the shield surface.

The interface angles of the inner ring and the spaces between the inner and outer rings defined by the linear ribs create a plurality of depots in these concavities for the spermicide to be retained. In addition, the ribs can be of hollow configuration forming a drug reservoir when filled with spermicide that flows out through specific portals during the flexing of the hollow rib which occurs during coitus with the retained spermicide being released and distributed within the vagina during such activity.

In use this unique shield is arced over into a U-shaped configuration when the opposite sides of the outer margins are opposed. The shield is inserted adjacent to the anterior and lateral walls of the vagina so to cover the cervix. Because the spermicide is applied to both sides, a spermicidal action is created between the shield and the cervix as well as directly on the surface area of ejaculation so that a dual contraceptive effect occurs, that of a physical barrier of the shield and a chemical (spermicidal) action of the drug.

By this mechanism there is an opportunity for maximization of sperm immobilization by the spermicide directly near the area of sperm ejaculation and the prevention of sperm migration around the vaginal shield, encountering again a spermicidal film, between the shield and the cervix.

The placement of the shield in the vagina with its dual spermicidal areas and its physical mechanical attribute of forming vaulted intimate physical contact through the soft conforming design of the shield acts to enhance the contraceptive efficiency of the product. These attributes are not available with any other vaginal contraceptive. During intercourse the spermicide is further distributed over the vaginal walls by the thrusting of the penis across the interface concavities. Thus, the spermicide is continuously distributed throughout intercourse providing greater contraceptive effectiveness. In addition, the spermicide within the reservoirs supplies a continual flow of spermicide to the surface providing continuous spermicidal action for prolonged periods. Further, mild stimulation of the male can occur by the interaction of the penis rubbing over the ribs of the supporting structure.

The special considerations of design of structure allows the shield contraceptive to be manufactured in mass quantities at low cost and therefore obtainable for use by a large segment of the population. Unlike the contraceptive commonly referred to as a diaphragm pessary, the shield of this invention may be used by any sexually active woman, nulliparous or parous, and requires no health professional for placement. The vaginal shield disclosed herein is intended for use only when intercourse is contemplated and to be disposed of afterwards. However, timing, insofar as insertion and removal of the device, is not critical so that its use does not distract from the pleasures of the moment.

User acceptance is enhanced by the following factors:
(1) one size for all women;
(2) thinness that allows multiple shields to be contained in a convenient purse package for ready availability;
(3) simple insertion without an applicator;
(4) the spermicide unit is totally self-contained without any additional preparations needed;
(5) immediate and prolonged action resulting from the film and reservoirs allows the user to utilize the product without inhibition of sponteneity of sexual activity with confidence of efficacy;
(6) provides sufficient spermicide stored within reservoirs which is only released with coitus so that it may be inserted at longer time intervals prior to coitus and eliminating the proximal timing needed with other vaginal products;
(7) free of the messiness of jellies, creams and suppositories because of the small volume of excipients and wide surface area of distribution on both sides of the shield;
(8) the physical attributes of the vaginal shield and the spermicide stored within its appropriate reservoirs allows for consecutive coital episodes without need for additional spermicide applications;
(9) is immediately available to provide protection whenever the woman elects to use it;
(10) is disposed of after each use and eliminates the unesthetic problems of cleaning and possibly damaging units that are designed to be reused;
(11) is free of metal springs and hence reduces the possibility for injury to either male or female tissues.

BRIEF DESCRIPTION OF THE DRAWINGS

FIG. 1 is a top view of a specific embodiment of the pessary of the present invention.

FIG. 2 is a side view, in section, of the specific embodiment of FIG. 1.

FIG. 3 shows the specific embodiment in its flexed, U-shaped configuration.

FIG. 4 is an enlarged partial sectional view of an alternative configuration of the outer ring.

FIG. 5 is an enlarged partial sectional view of another alternative configuration of the outer ring.

FIG. 6 is a top view of an alternative embodiment of the present invention.

DETAILED DESCRIPTION OF A SPECIFIC EMBODIMENT

At FIG. 1 a shield 2 is shown having an outer ring 4, an inner ring 6, six generally evenly spaced connecting ribs 8, all bonded to a thin flexible film 10. These rings and ribs may be of the same cross-sectional dimensions. As shown in FIG. 2, the outer and inner rings have a hemispherical cross-sectional shape and are bonded, such as by heat sealing, to film 10 along their flat bottom surfaces 5, 7. The outer ring is preferably between 70 and 110 mm in diameter while the inner ring shown in this embodiment has a diameter which is typically 40 to 85%, usually 60 to 80%, of the diameter of the outer ring. The outer ring is typically 0.5 to 4 mm thick and 2 to 5 mm wide. The width and thickness of the inner ring and the ribs are preferably equal to or somewhat less than, but usually not less than about half the corresponding dimensions of the outer ring. The film is preferably between about 1–4 mils thick.

The material or materials from which the shield of this invention are formed are non-reactive and preferably are heat sealable and injection moldable. Further, the circular ribs (rings), the linear ribs and the film should be flexible but not elastomeric. It has been found that the combination of a relatively non-elastic but flexible film and a flexible, somewhat soft supporting structure provides a unique U-shaped bow configuration when the opposite edges of the ring are bent toward each other for placement within the vagina. The somewhat soft and flexible supporting structure allows for increased comfort for the female and increased pleasure for the male during coitus. This configuration is shown in FIG. 3.

The bow produced stores the molecular energy of plastic deformation and insures that the shield remains adjacent to the walls of the vagina by the continuous force to resume the original planer configuration, thereby enhancing the intimacy of physical vaginal shield contraceptive contact with the vaginal wall.

The vaginal shield preferably has a spermicide applied to both sides. The preferred approved spermicide to be used at this time is nonoxynol 9. This is dispersed in a polyethylene glycol of about 1,000 to 10,000 units, more usually about 2,000 to 6,000 units, e.g., PEG 4,000, to provide for the desired consistency. About 50 to 100 mg of nonoxynol 9 will be present with each shield. The spermicide is typically applied by spraying or dipping onto the lower surface 12 of the film as well as applied to the upper surface 13 of the film within concavities 14, 16 and over the rings and ribs. Concavities 14 are the spaces bounded by the inner and outer rings, the ribs and the upper surface of the film. Concavity 16 is the space bounded by the inner ring 6 and the upper surface of the film. The applied material will have increased quantities deposited at the concavities 15 formed by all interfaces of the film with the ribs or rings.

Alternative structures for holding and releasing additional spermicide are shown in FIGS. 4 and 5. In FIG. 4 the outer ring 18 has a tunnel cross-section with an annular groove or void 20 and a base 19 in contact with the film 10. A plurality of openings 22 are formed through the top arcuate surface 21 for communication with groove 20. The annular groove provides a reservoir of spermicide which is released into the vagina during coital activity since the tunnel rings are deformable. FIG. 5 shows outer ring 24 intermittently bonded to film 10 along its base 25 thus providing a plurality of passageways 26 communicating with the annular groove 28. The groove and passageways of the configuration of FIG. 5 act in the same manner as groove 20 and openings 22 of the configuration of FIG. 4. The upper surface 29 of ring 24 is serrated or grooved to provide further spaces to hold a quantity of spermicide to be released during coitus. If desired the surface of the connecting ribs or the inner ring can be roughened as with ribs or grooves in a like manner as ring 24.

Other embodiments may have one outer ring with cross connecting ribs, multiple concentric rings with or without connecting ribs, a continuous spiral ring from margin to center, or a single outer ring with a waffle center pattern. All of such embodiments provide for spermicidal reservoirs over the surface of the shield as well as the ability to exert the gentle pressure against the vaginal walls to maintain intimate contact. FIG. 6 shows an alternative embodiment having an egg-shaped outer ring 35 and a spiral inner member 37.

Although six connecting ribs are shown in the specific embodiment of FIG. 1, as few as two connecting ribs and as many as 10 ribs are contemplated. The connecting ribs serve to register the inner ring prior to bonding to the film, provides a mechanical form that produces the unique configuration on compression and act as reservoirs for placement of spermicide. Inner and outer rings are shown circular, however other, preferably arcuate, shapes such as elliptical, helical, or crescentic may be employed if desired.

Other supporting structures, aside from rings and connecting ribs, may be used to provide the dual functions of defining spermicidal reservoirs and insuring that the film abuts the vaginal wall. Thus, the spiral inner members of the embodiment shown in FIG. 6 perform the same reservoir-defining and vaginal wall conforming functions as the connecting ribs and inner ring of the embodiment shown in FIG. 1.

Briefly the vaginal shield is produced according to the following steps. The outer and inner rings and the connecting ribs are formed by injection molding or by stamping as a single structural member. The structural member is then dropped onto the film and heat sealed thereto. Excess film around the outer ring can be removed by flashing or turning. The spermicide is then sprayed onto both sides of the film. The spermicide mixture is preferably applied in a semi-liquid state at temperatures of about 50° C. and on cooling to below 36° C. adheres to the film. This specific melt temperature is achieved by the selection of the appropriate unit length of propylene glycol and its weight ratio to the liquid nonoxynol 9. A greater amount of spermicide is applied to the upper surface of the film and is held within concavities 14 and 16. If, however, the outer ring has an annular groove as disclosed in FIGS. 4 or 5, the groove is filled with spermicide before the supporting structure is bonded to the film. The polyethylene glycols are found to be compatible with the heat sealing of ethylene polyvinyl acetate rings to film of the same composition. Methods of bonding other than heat sealing may be employed.

The use of the vaginal shield contraceptive is straight-forward. The user arcs the unit into a generally U-shaped configuration that is inserted into the vagina so that the outer surface of the film lies adjacent to the anterior and lateral walls of the vagina. The interior structural members insure that the film substantially abuts the vaginal walls when so placed. The spermicide on the outer surface 12 of the film is thereby distributed over the vaginal walls it is contacting. Coital activity causes the spermicide in concavities 14, 16 to be fully distributed over the vaginal walls. If an annular groove 20 is provided, the spermicide is also released therefrom during coitus. Thus, effective distribution of spermicide is accomplished before and during coitus. As a result of the wide surface of distribution and the thin layer of the spermicide-polyethylene glycol mixture, the mixture melts rapidly and the contraceptive action is available immediately upon insertion.

Although a specific embodiment has been shown and described above, modification and variation may be made without departing from what is regarded as the subject of the invention.

What is claimed is:

1. A contraceptive vaginal shield comprising:
    a circumferential plastic flexible non-elastomeric rod-like supporting member;
    a thin non-elastomeric film bound to said supporting member and relatively tautly extending over the area enclosed by said circumferential supporting member;
    at least one internal flexible plastic rod-like supporting member bonded to said non-elastomeric film for providing structural support for said non-elastomeric film; and
    wherein said supporting member and film define at least one spermicidal reservoir and when said shield is bent into a U-shaped configuration and inserted into the vagina, the restoring forces of said flexible rod-like supporting member maintains said non-elastomeric film in juxtaposition to the vaginal wall.

2. The contraceptive vaginal shield according to claim 1, wherein at least a portion of said shield is coated with a spermicide.

3. The contraceptive vaginal shield according to claim 1 wherein the film is heat sealed to the rod-like supporting member.

4. The contraceptive vaginal shield according to claim 1 wherein the film is integrally formed with said rod-like supporting member.

5. The contraceptive vaginal shield according to claim 1 wherein the rod-like supporting members are hollow and function as a reservoir for storing spermicidal agent.

6. The contraceptive vaginal shield according to claim 1 wherein the rod-like supporting members are solid with grooved surfaces.

7. The contraceptive vaginal shield according to claim 1 wherein the rod-like supporting member includes inner and outer concentric rings.

8. A contraceptive vaginal shield comprising:
    a supporting member including inner and outer concentric spaced apart flexible rings, said rings having generally curved upper surfaces and generally flat lower surfaces and from 2 to 10 flexible connecting ribs extending between said rings;
    a thin flexible non-elastomeric film bound along a first face to the lower surfaces of said rings and ribs and tautly extending over the area defined by said outer ring;
    a spermicide contacting at least a portion of said first face of said film; and
    wherein when said shield is bent into a U-shaped configuration and inserted into the vagina the restoring forces of said supporting member maintains said flexible non-elastomeric film in juxtaposition to the vaginal wall.

9. The vaginal shield of claim 8 wherein said outer ring is circular and said film is heat sealed to said lower surfaces of said rings.

10. The vaginal shield of claim 8 wherein said spermicide contacts the opposing face of said film.

11. The vaginal shield of claim 9 wherein said outer ring has a diameter of about 70 to 110 mm and is about 0.5-4 mm thick and about 1-5 mm wide.

12. The vaginal shield of claim 8 wherein said rings, said ribs and said film is ethylene vinyl acetate copolymer having about 4-16% vinyl acetate mol percent.

13. The vaginal shield of claim 8 wherein said spermicide comprises a semi-solid polyethylene glycol.

14. A contraceptive vaginal shield comprising:
a supporting structure comprising a circumferential flexible, rib supporting member and at least one internal flexible non-elastomeric rib supporting member connected to said circumferential member at at least one point;
a flexible thin non-elastomeric film bound to one side of said supporting structure and tautly extending over the area defined by said circumferential member;
wherein said supporting structure and film define at least one spermicide reservoir and when said shield is bent into a U-shaped configuration and inserted into the vagina, the restoring forces of said supporting structure maintains said non-elastomeric film in juxtaposition to the vaginal wall.

15. The vaginal shield of claim 14 wherein said internal flexible member includes a plurality of linear ribs.

16. The vaginal shield according to claim 13 wherein said supporting structure is grooved within at least a portion of said rib supporting members, said groove communicating with the exterior of said supporting structure for release spermicide contained therein when said supporting structure is deformed.

17. A method for producing a vaginal contraceptive comprising
forming a flexible, generally planar framework, said framework comprising at least an outer ring and an inner member defining at least one reservoir space within said outer ring;
bonding at least a portion of one side of said framework to a thin flexible film to tautly extend over the area defined by said outer ring; and
applying a spermicide to at least one side of said film.

18. The method according to claim 17 wherein said forming step includes the step of forming by extruding said framework.

19. The method according to claim 17 wherein said applying step includes the step of applying said spermicide to both sides of said film.

20. The method according to claim 17 where said forming step provides a framework including
a groove along a first surface of said outer ring, said groove having means for fluidly communicating with the exterior of said outer ring; and said forming step includes the steps of:
placing a quantity of said spermicide within said groove prior to said bonding step; and wherein said bonding step includes the step of:
bonding said first surface of said outer ring to said film, thereby partially enclosing said spermicide between said outer ring and said film.

* * * * *